United States Patent
Fayram et al.

(10) Patent No.: US 6,826,427 B1
(45) Date of Patent: Nov. 30, 2004

(54) METHODS AND DEVICES FOR INHIBITING BATTERY VOLTAGE DELAYS IN AN IMPLANTABLE CARDIAC DEVICE

(75) Inventors: Timothy A. Fayram, Gilroy, CA (US); Mark W. Kroll, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 477 days.

(21) Appl. No.: 10/054,468

(22) Filed: Jan. 18, 2002

(51) Int. Cl.[7] ............................................. A61N 1/39
(52) U.S. Cl. ..................................... 607/29; 607/5
(58) Field of Search ........................... 607/1–5, 7, 9, 607/27, 29

(56) References Cited

U.S. PATENT DOCUMENTS

| | | | |
|---|---|---|---|
| 5,411,537 A | 5/1995 | Munshi et al. ................. 607/33 |
| 5,899,923 A | 5/1999 | Kroll et al. ..................... 607/5 |
| 5,904,705 A | 5/1999 | Kroll et al. ..................... 607/5 |
| 5,959,371 A | * 9/1999 | Dooley et al. ................. 607/5 |
| 6,283,985 B1 | 9/2001 | Harguth et al. ................ 607/1 |

* cited by examiner

*Primary Examiner*—George R. Evanisko
(74) *Attorney, Agent, or Firm*—Steven M. Mitchell

(57) ABSTRACT

A battery of a cardiac stimulation device may experience voltage delay problems caused by a passivation layer that forms on the anode of the battery. To inhibit voltage delay, the battery is periodically used to charge the capacitor to a partial charge. Both the charge time and the interval between charges can be adjusted to reduce the power consumption required to inhibit battery voltage delay.

15 Claims, 10 Drawing Sheets

METHODS AND DEVICES FOR INHIBITING BATTERY VOLTAGE DELAYS IN AN IMPLANTABLE CARDIAC DEVICE

BACKGROUND OF THE INVENTION

1. Field of the Invention

The present invention relates generally to implantable cardiac devices, such as implantable cardioverter defibrillators (ICDs). The present invention more particularly relates to inhibiting voltage delay in a battery of an implantable cardiac device.

2. Background Art

Implantable cardiac devices, such as implantable cardioverter defibrillators (ICDs), are well known in the art. Such devices are generally implanted in a pectoral region of the chest beneath the skin of a patient within what is known as a subcutaneous pocket. The primary components of an ID include a monitoring and detection mechanism, a capacitor, a battery, a sensing system for detecting an arrhythmia, and a control system for controlling delivery of a capacitive discharge electrical shock in response to a detected arrhythmia by charging and then discharging the capacitor. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

Implantable devices, such as ICDs, pose a unique demand on the battery power supply. The battery must be capable of operating at low current drains for long periods of time, and simultaneously be capable of providing high current pulses. The battery must sustain the provision of the high current pulses and must be available whenever a patient requires defibrillation.

Batteries that are used in current ICD's can develop high internal impedance or equivalent series resistance (ESR) over the lifetime of the ICD. This is undesirable because a battery with an excessively high ESR will ultimately be unable to deliver sufficient current to the circuitry of the ICD leading to a potentially catastrophic result to the patient. Batteries with an ESR that is higher than normal also take longer to charge the capacitor of the ICD, thus potentially delaying the delivery of vital therapy to the patient. Under normal operations, a battery in an ICD should be capable of charging a capacitor in less than about fifteen seconds. Batteries with a higher than normal ESR may take twice as long. Note, many ICD's are programmed to "time out" after a certain charge time to save energy. For example, an ICD's may be programmed to stop capacitor charging after 30 seconds. The time interval at the start of a discharge during which the working voltage of a battery cell is below its steady value (which is caused by the higher than normal ESR) is referred to as the "voltage delay." ESR will also increase when the battery is completely discharged. However, this ESR is not associated with voltage delay which is normally a phenomenon that occurs in the middle of the discharge curve.

Accordingly, it is imperative to limit the development of a high ESR in ICD batteries to thereby inhibit voltage delay. Generally, when a battery reforms a capacitor on a periodic basis, the battery system itself reduces its ESR through the usage. While this technique is effective in reducing battery ESR, it should not be used more often than about once a month because the process is extremely energy-inefficient. For example, each reforming charge of the capacitor may require the withdrawal of 30–40 joules of energy from the battery. If this is performed on a regular schedule to limit ESR development in the battery, it would squander a large amount of battery energy.

While existing ICD batteries have proven effective, it would be desirable to improve the effectiveness and efficiency of ICD batteries by limiting ESR development in ICD batteries such that the batteries are maintained at a predetermined ideal state of voltage and current delivery capacity. In other words, it is desirable to inhibit battery voltage delay in a manner that wastes as little battery energy as possible.

BRIEF SUMMARY OF THE INVENTION

The present invention is directed towards methods and devices for inhibiting voltage delay in a battery of an implantable cardiac stimulation device. These methods and devices of the present invention can also be used to reform a capacitor of the implantable cardiac stimulation device. Such a capacitor (which is typically implemented as two capacitors in series for increased voltage handling capability) is charged using the battery. The charge on the capacitor can then be used to shock the heart of the patient within which the stimulation device is implanted. If the capacitor was charged for a reason other than for delivering a shock (e.g., for inhibiting battery voltage delay and/or reforming the capacitor), then the charge on the capacitor can be allowed to slowly dissipate or discharged using a dump circuit.

According to an embodiment of the present invention, the capacitor begins to be charged at a time determined based on a comparison between a time since a last charge of the capacitor and a threshold time between charges. For example, the capacitor may begin to be charged when the time since the last charge of the capacitor equals the threshold time between charges. A charge on the capacitor is then measured at a predetermined time since the capacitor began charging. The capacitor continues to be charged until a threshold charging time since the capacitor began charging is reached, at which point charging stops. The threshold charging time is then adjusted based on the measured charge on the capacitor. This threshold charging time can be adjusted prior to or after the stopping of the charging of the capacitor.

In an alternative embodiment, rather than adjusting the threshold charging time, the threshold time between charges is adjusted based on the measured charge (i.e., voltage) on the capacitor. In another embodiment, both the threshold charging time and the threshold time between charges are adjusted.

BRIEF DESCRIPTION OF THE FIGURES

Further features and advantages of the present invention may be more readily understood by reference to the following description taken in conjunction with the accompanying drawings, in which.

DETAILED DESCRIPTION OF THE INVENTION

The following description is of the best modes presently contemplated for practicing the invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

Exemplary Stimulation Device

Figure 1:
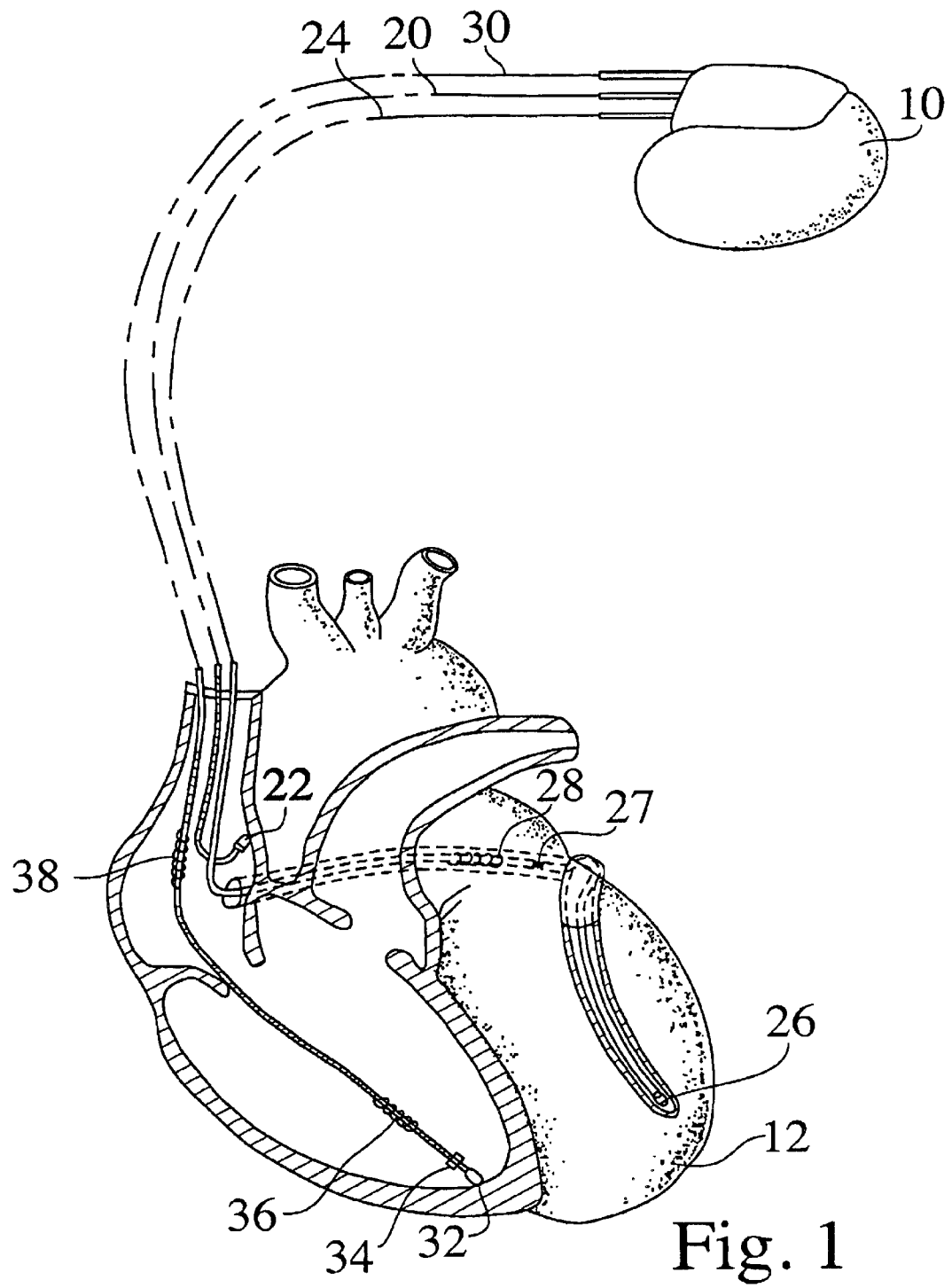
FIG. 1 is a simplified diagram illustrating an implantable stimulation device in electrical communication with at least three leads implanted into a patient's heart for delivering multi-chamber stimulation and shock therapy.

FIG. 1 shows an exemplary implantable cardiac stimulation device 10 (also referred to as a pacing device, a pacing apparatus, or an ICD) in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
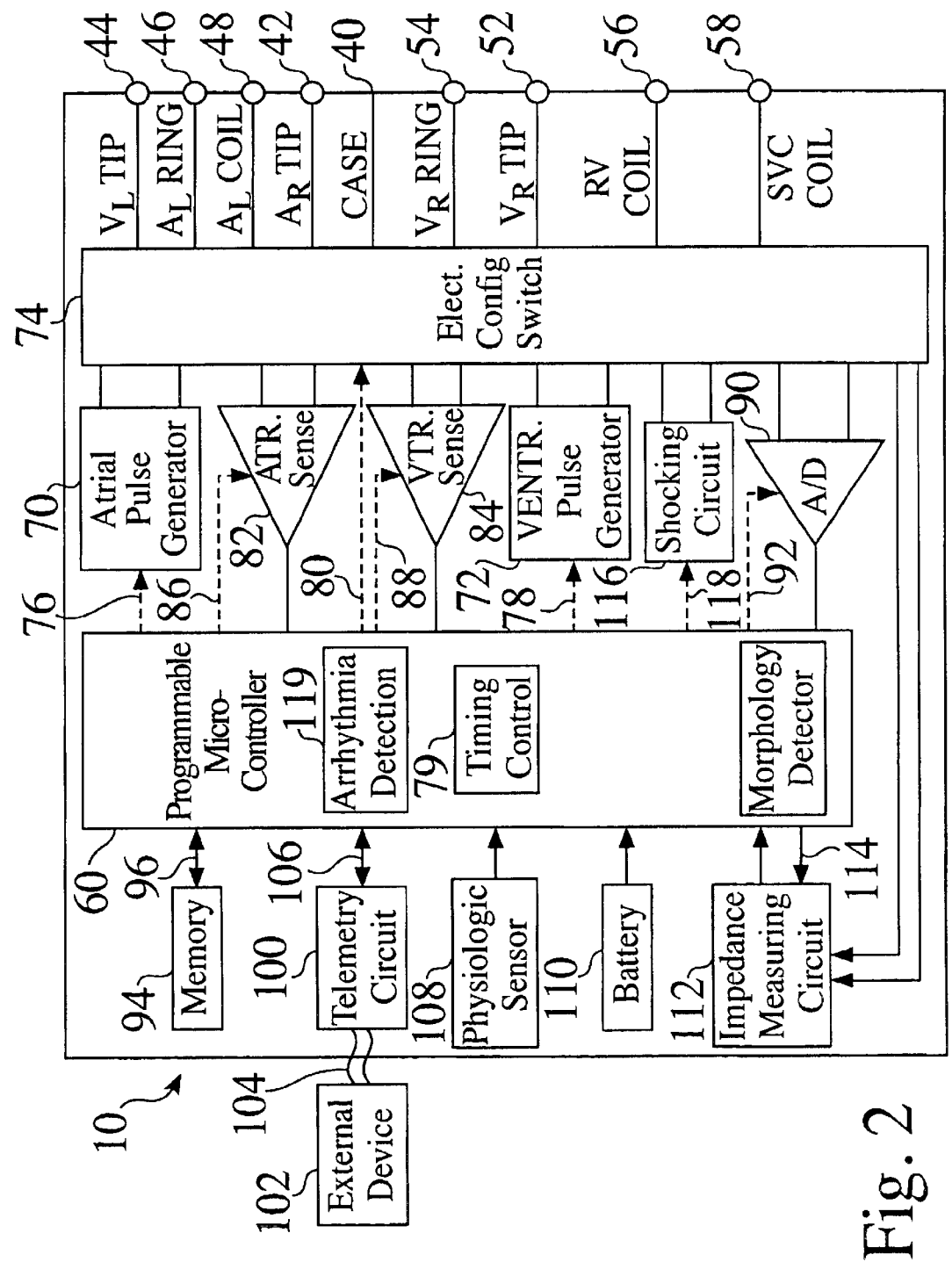
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the stimulation device and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to, atrio-ventricular (AV) delay, interventricular (RV-LV) delay, atrial interconduction (A—A) delay, ventricular interconduction (V—V) delay, and pacing rate.

The switch bank 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart. The sensing circuits 82 and 84, in turn, receive control signals over signal lines 86 and 88 from the microcontroller 60 for purposes of measuring cardiac performance at appropriate times. The sensing circuits 82 and 84 also control the gain, threshold, polarization charge removal circuitry (not shown), and timing of any blocking circuitry (not shown) coupled to the inputs of the sensing circuits 82 and 84.

For arrhythmia detection, the device 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60. Microcontroller 60 classifies the timing intervals by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). A sensing system of the present invention, for example, is implemented in the arrhythmia detection 119 software and/or hardware of microcontroller 60. The sensing system can also include, for example, sensing circuits 82 and/or 84, discussed above.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse. Microcontroller 60 starts a capture detection window using the timing control circuitry 79 within the microcontroller 60. Additionally, microcontroller 60 enables the data acquisition system 90 (via control signal 92) to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to an external device 102 through an established communication link 104.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (McClure et al.), which patents are hereby incorporated herein by reference.

The stimulation device 10 can also include a physiologic sensor 108, that can be used to detect changes in cardiac performance or changes in the physiological condition of the heart. Accordingly, the microcontroller 60 can respond by adjusting the various pacing parameters (such as rate, AV Delay, RV-LV Delay, V—V Delay, etc.) in accordance with the embodiments of the present invention. The microcontroller 60 controls adjustments of pacing parameters by, for example, controlling the stimulation pulses generated by the atrial and ventricular pulse generators 70 and 72. While shown as being included within the stimulation device 10, it is to be understood that the physiologic sensor 108 may also be external to the stimulation device 10, yet still be implanted within or carried by the patient. More specifically, the sensor 108 can be located inside the device 10, on the surface of the device 10, in a header of the device 10, or on a lead (which can be placed inside or outside the bloodstream). The sensing system of the present invention can include, for example, physiological sensor 108.

The stimulation device 10 additionally includes a battery 110 which provides operating power to all of the circuits shown in FIG. 2. When performing shocking therapy, the battery 110 must be capable of minimal self discharge when inactive, capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium silver vanadium oxide batteries, as is true for most current devices. The control system of the present invention, which can be implemented by microcontroller 60, can control the delivery of current from battery 110.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown only for completeness.

Stimulation device 10 can detect the occurrence of an arrhythmia, and apply appropriate electrical shock therapy to the heart aimed at terminating the detected arrhythmia. To this end, the microcontroller 60 further controls a shocking circuit 116, for example, by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, the microcontroller 60 is capable of controlling the synchronous or asynchronous delivery of the shocking pulses.

Exemplary Shocking Circuit

Figure 3:
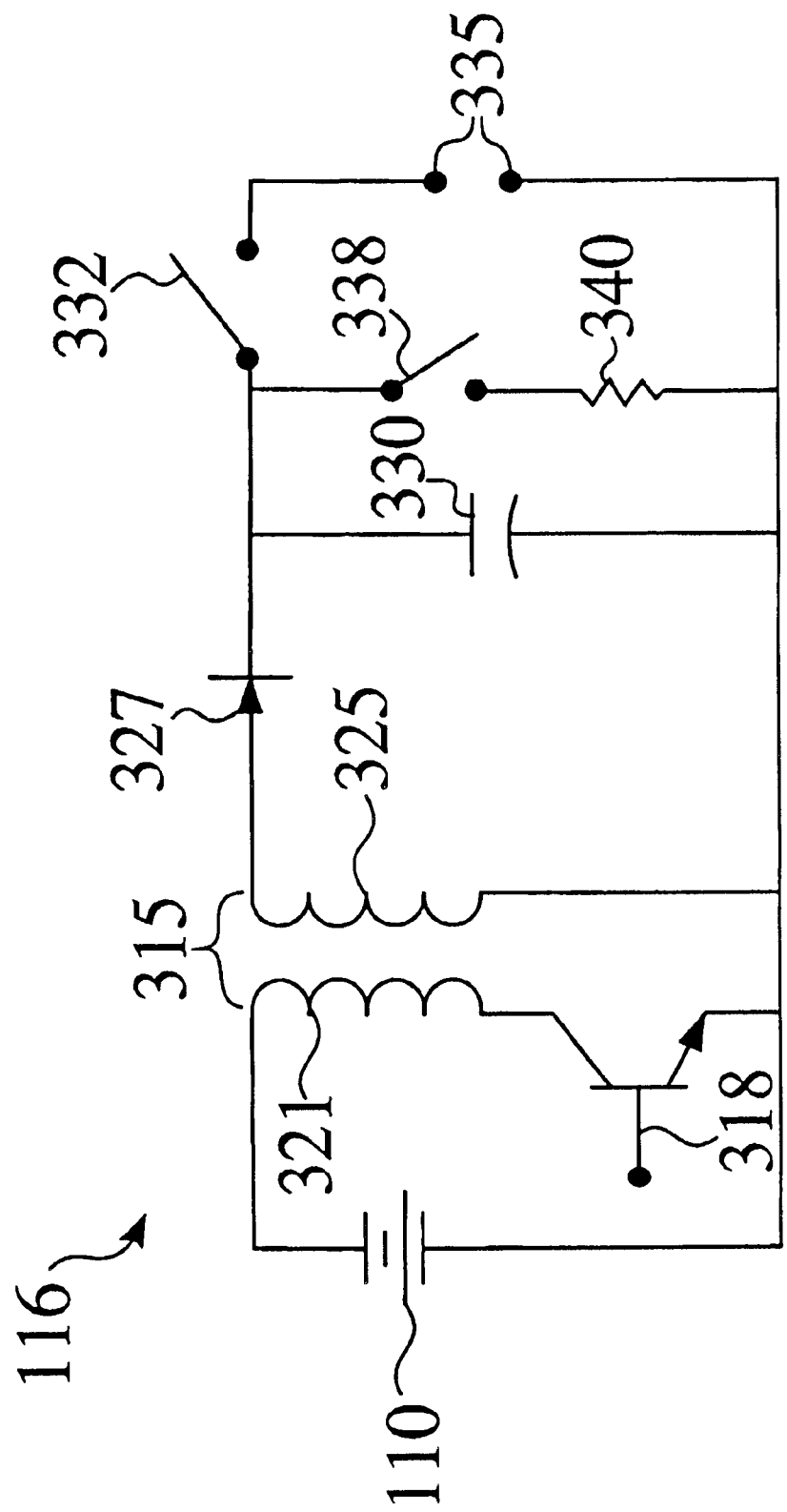
FIG. 3 is a diagram of an exemplary shocking circuit that can be used in an embodiment of the present invention.

FIG. 3 is a simplified diagram of an exemplary shocking circuit 116 of stimulation device 10. Exemplary circuit 116 is coupled to the battery 110 of device 10, which is typically a Lithium-Silver Vanadium Oxide (SVO) battery. Exemplary circuit 116 includes a transformer 315, which includes a primary winding 321 and a secondary winding 325. Battery 110 provides a current through primary winding 321 of transformer 315. A switching transistor 318 drives primary winding 321. More specifically, switching transistor 318 provides an alternating current through primary 321 by cycling the current on and off at a high rate (e.g., 100 to 500 kHz). Secondary winding 325 of transformer 315 produces a significantly higher voltage which is rectified by a diode 327 and stored in a capacitor 330.

For defibrillation of the heart, when capacitor 330 is fully charged, a switch 332 (e.g., a semiconductor switch) is activated (i.e., closed) to complete the circuit which delivers the charge of capacitor 330 to the appropriate cardiac electrodes 335 (e.g., selected from the left atrial coil electrode 28, the RV coil electrode 36, and/or the SVC coil electrode 38). A configuration which is similar to the above circuit includes an H-bridge in place of switch 332. This permits delivery of the current from capacitor 330 in either polarity, which allows delivery of a biphasic pulse. Switching transistor 318 and switch 332 can be controlled by a control system, which can be implemented by microcontroller 60. It is noted that capacitor 330 may represent a plurality of parallel capacitors, as would be appreciated by one of ordinary skill in the art. Additionally, battery 110 may represent a plurality of serially connected cells, as would also be appreciated by one of ordinary skill in the art.

A dump circuit can be used to discharge a charge on capacitor 330 without stimulating the heart. An exemplary dump circuit includes an internal resistor 340 and a switch 338. When switch 338 is closed (and 332 is open) a charge on capacitor 330 will be discharged across resistor 340 without stimulating the heart.

The above description provides an example of a shocking circuit that can be used with the present invention. Those of ordinary skill in the relevant art will appreciate that other shocking circuits can be used while still being within the spirit and scope of the present invention.

Exemplary Battery Characteristics

The most common type of battery 110 in a present implantable stimulation device 10 is a Lithium-Silver Vanadium Oxide (SVO) battery. In such a battery design, the active cathode material is silver vanadium oxide. Silver vanadium oxide belongs to a class of nonstoichiometric compounds known as vanadium oxide bronzes. These compounds are semiconductors and exhibit tunnel-like crystal structures which provide diffusion paths for metal ions. It has been demonstrated that an optimum composition of the cathode material is $Ag_2 V_4 O_{11}$. Cell discharge takes place in multiple steps. The first two steps, which occur simultaneously, are the reduction of vanadium (V) to vanadium (IV) and the reduction of silver (I) to silver (0). The final step is the reduction of vanadium (IV) to vanadium (III). Because of the reduction of silver to the metallic state, the conductivity of the cathode increases during discharge. Stoichiometrically, one mole of $Ag_2 V_4 O_{11}$ can react with a total of seven moles of lithium.

Figure 4:
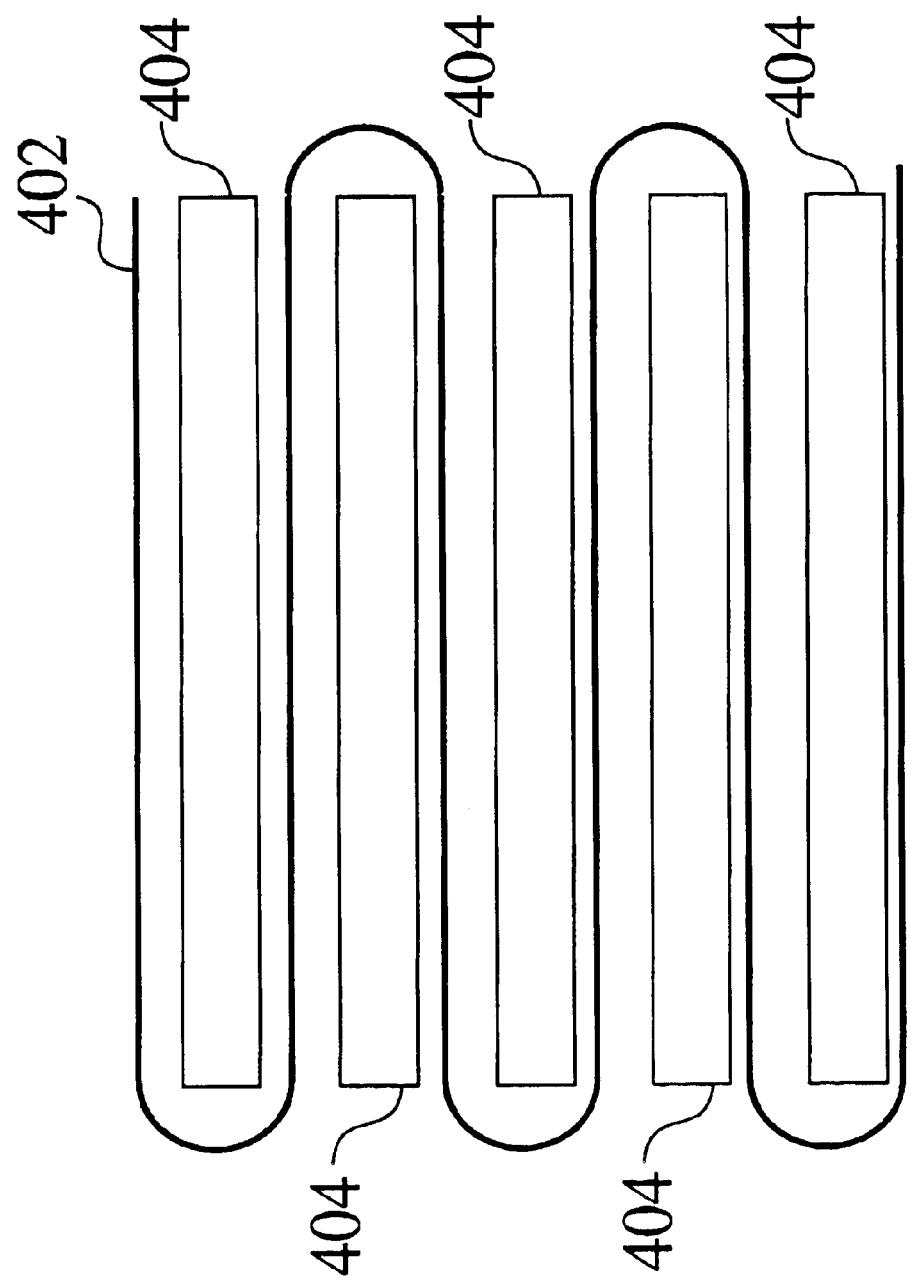
FIG. 4 is a conceptual illustration of a cell design.

The anode in an SVO cell is typically pure lithium metal pressed onto a nickel current collector. The cathode material is typically a mixture of silver vanadium oxide, a Teflon binder, and a conductive carbon material. Individual cathode plates are formed by pressing the cathode material onto a metal current collector to produce a structurally sound pellet. The pellet contains 95% live cathode material. As illustrated conceptually in FIG. 4, the anode 402 is typically folded into an "accordion" design, and individual cathode plates 404 are typically placed between each "fold" of the anode. Both anode 402 and cathode plates 404 are enclosed in an organic separator for redundancy.

The chemical reactions occurring in the cell result in a constantly changing chemical composition of the cathode as the cell reaction proceeds, with a resultant change in the energetics of the reaction. This phenomenon leads to a discharge curve which exhibits plateaus at various voltages and a general gradual decline in the voltage as normal battery discharge proceeds over extended periods of time. This is discussed below in more detail in connection with FIG. 6. The present invention recognizes that it is possible to assess the state of discharge of the cell by interrogating the cell voltage during discharge (e.g., using a voltmeter in parallel with battery 110).

Figure 5:
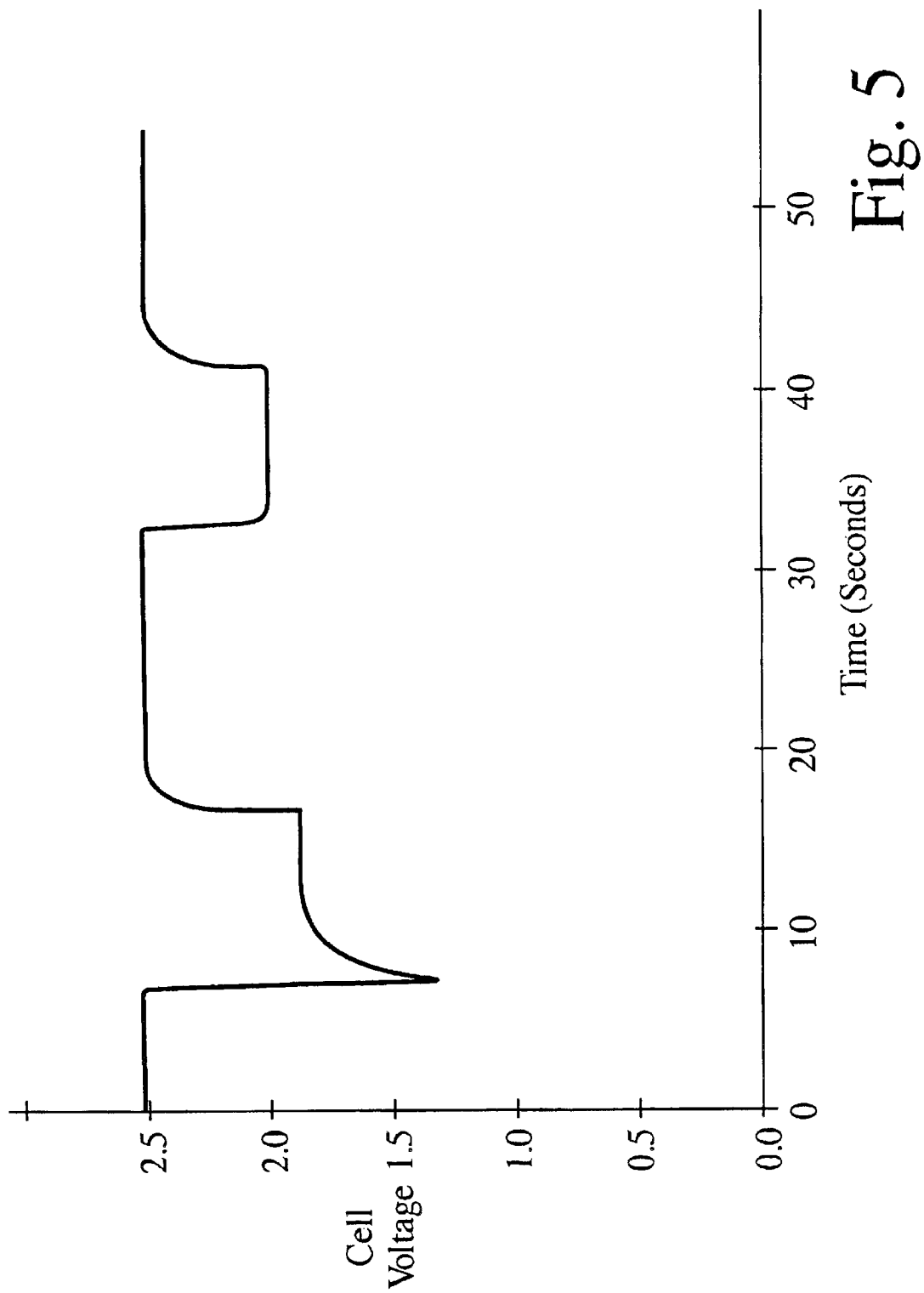
FIG. 5 is a plot of a cell voltage vs. time during two simulated charging cycles illustrating a case of severe voltage delay indicative of a high ESR condition.

In FIG. 5, a sample plot of voltage vs. time for an ICD with circuitry of the type in FIG. 3 is shown. Battery 110 was left unattended for several months. At the start of capacitor charging, battery 110 had an open circuit voltage of 2.51 V which decreased to 1.35 V. During the charging, the voltage gradually recovered to 1.91 V. After a 15 second rest period, another charging cycle was initiated which had an initial voltage of 2.00 V. Thus, battery 110 had recovered to normal operation for the second capacitor charging cycle. However, the charging performance during the first cycle was well below expected performance characteristics for an ICD. In a clinical setting, such a delay in application of a countershock from the ICD's capacitors could have potentially disastrous consequences for the patient in whom the device is implanted. The data of FIG. 5 illustrate the effects of failure to maintain an SVO battery and the consequent development of an equivalent series resistance (ESR) condition in the battery. The observed phenomenon during the initial charging cycle can be prevented by periodic capacitor charging, currently necessary for capacitor "reforming."

However, as the design and fabrication of capacitors continues to improve, the requirement for periodic capacitor "reforming" may eventually become unnecessary, and there may be no other need for this regular and highly inefficient use of stored battery energy.

Figure 6:
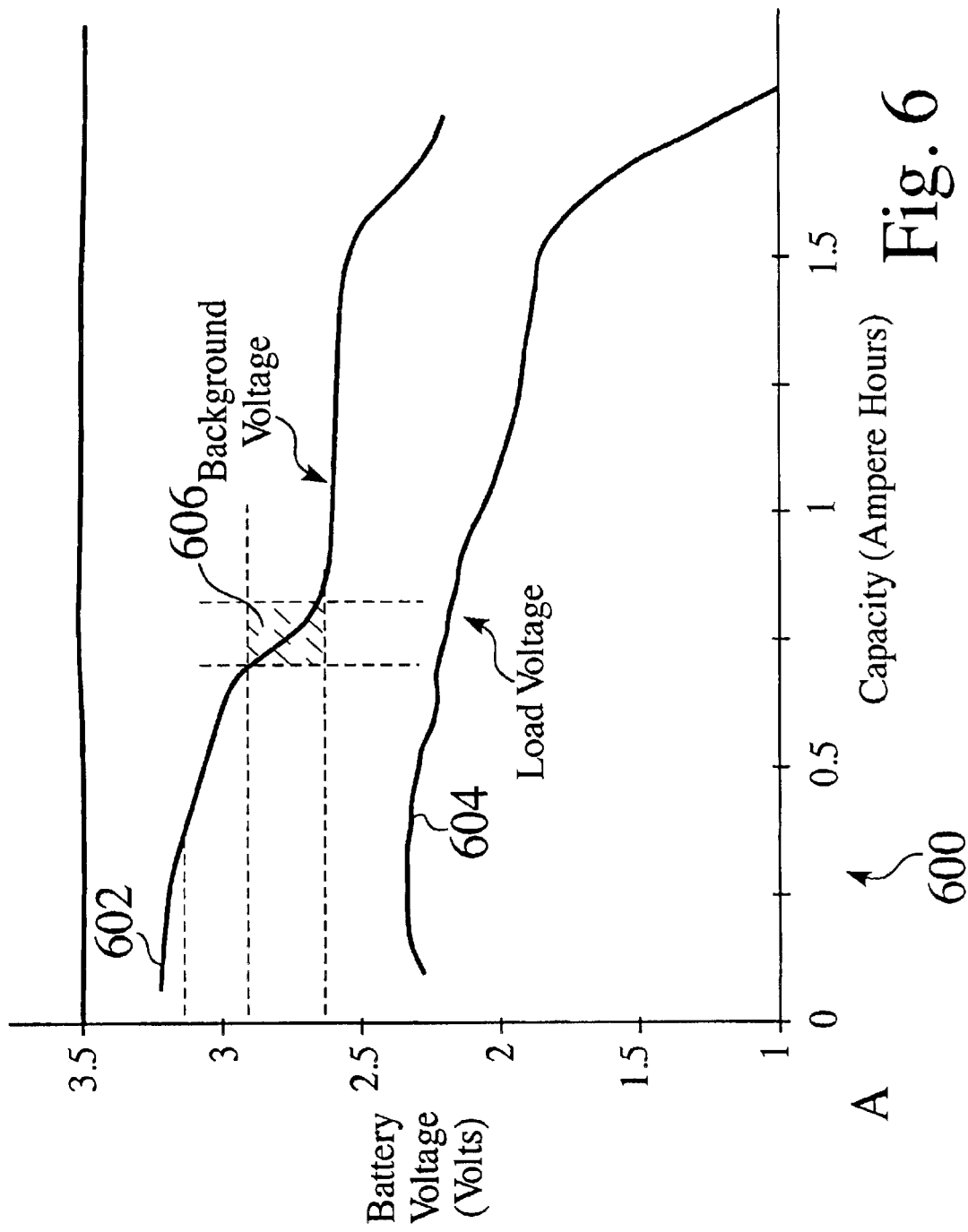
FIG. 6 is a graphical representation of a battery voltage versus delivered charge for both an unloaded and a loaded circuit.

FIG. 6 is a graph 600 illustrating the typical discharge behavior for SVO battery 110. The vertical axis of graph 600 specifies a voltage of battery 110. The horizontal axis of graph 600 illustrates the charge delivered by battery 110 in ampere hours (Ah). An uppermost curve 602 represents the battery voltage during normal monitoring and pacing activities. This curve 602 is often referred to as the "unloaded voltage" or the "background voltage." Curve 602 is also sometimes referred to as the "open circuit voltage" as it is a measure of the voltage while the cell is under a small or nonexistent load. (The monitoring current is very small compared to the load during capacitor charging.) A lowermost curve 604 represents the voltage of battery 110 when capacitor 330 is being charged (i.e., when the battery is under a load and is delivering its maximum current). This is often referred to as the "load voltage" or "loaded voltage." The loaded voltage is less than the open circuit voltage (i.e., curve 602) by about 0.6 V since the ESR of the cell is about 0.3 Ω. (and 0.6V=2A×0.3 Ω, by Ohm's law). The ESR represents the internal resistance of the cell which causes its loaded voltage to be less than its open circuit voltage. It is the unloaded voltage (i.e., the uppermost curve 602) that is typically monitored by the ICD and typically reported by a telemetry means.

The shape of curve 602 (i.e., the unloaded voltage) is relatively independent of ICD model and manufacturer. As shown in FIG. 6, curve 602 gently slopes from about 3.25 V at the beginning of the batteries life to about 3.15 V. This is followed by a region of slightly more rapid decline from about 3.15 V to about 2.9 V. In this region (i.e., the voltage range of about 3.25 to 2.9 volts), an ICD designer would expect the most responsive performance from the battery. This is often referred to as the region where the Silver is being expelled from the cathode crystalline structure and is replaced by Lithium supplied from the anode.

After most or all of the Silver is expelled, one observes an increase in the negative slope of curve 602, from about 2.9 volts to 2.6 volts. This relatively steep transition region 606 is the region of the discharge curve where the battery is most susceptible to the anode passivation layer that forms on the surface of the battery anode and causes a "voltage delay" phenomenon, which is discussed in some more detail below.

Following this relatively steep region 606, the slope of curve has a very flat "plateau" for the next period of time. Finally, this voltage again decays at a fairly linear rate. An elective replacement indicator (ERI) voltage is selected by the ICD designer, typically around 2.4 volts.

In the relatively steep region 606 (i.e., between about 2.9 V and 2.6 V, for the example of FIG. 6), a build up of impedance can occur under battery operating conditions of infrequency use. This causes a "voltage delay," which refers to the time interval at the start of a discharge during which the working voltage of battery 110 is below its steady value. The phenomenon is generally due to the presence of passivating films on the negative electrode (e.g., anode 402). While operating in the relatively steep region 606, battery 110 can experience as much as a 50% reduction in power (volts x amperes) to the input of the shocking circuit (e.g., circuit 116 shown in FIG. 3), thereby negatively impacting (i.e., significantly increasing) the high voltage charge time of an ICD. This phenomenon is inherent to SVO battery chemistry. It only occurs in the relatively steep transition region 606 when battery 110 is infrequency pulsed, and disappears as the battery in further discharged (i.e., in the region of curve 602 following the upper end of steep transition region 606).

With voltage delay, the cell voltage at the start of a capacitor charging cycle is lower than at the end. As illustrated in FIG. 5, during a 10 second charging cycle, the voltage rises from an initial minimum voltage during the first 2 or 3 seconds of the pulse and then continues at the typical pulse voltage throughout the rest of the 10 second interval. This phenomenon is exacerbated as the length of time between pulses increases. As shown in FIG. 5, the voltage delay can lead to a significant voltage decrease during the start of charging.

If battery 110 is pulsed monthly or more frequently, the voltage delay phenomenon is not observed. Accordingly, one conventional method for avoiding voltage delay is to fully charge capacitor 330 on a monthly basis, thereby preventing the passivating films from forming on the negative electrode of battery 110 and avoiding the voltage delay phenomenon. The charge is then allowed to slowly bleed off or may be dissipated using a dumping circuit (e.g., including an internal resistor 340). A problem with this approach is that approximately 50 joules of energy per month are wasted, thereby significantly reducing the life span of battery 110. The present invention is related to an improved method for inhibiting voltage delay with reduced energy dissipation from battery 110. Thus, the present invention can be used to inhibit voltage delay without significantly reducing the life of battery 110.

The above-described method of fully charging capacitor 330 once a month to avoid voltage delay is also used to reform capacitor 330 (i.e., reform the $Al_2O_3$ dielectric layer in capacitor 330). However, this method is not optimal because most deformation of capacitor 330 typically occurs in about the first 7 days after reforming, and then quickly reaches equilibrium. In the present invention, deformation of capacitor 330 is reduced because capacitor 330 is charged more often, as will be described below.

Assume capacitor 330 charges at about 5 joules/second. In the present invention, as will be described below, capacitor 330 is charged more frequently, but typically for a shorter period of time. More specifically, in the present invention, capacitor 330 is charged once about every 5 to 10 days (preferably, once about every 10 days). Thus, in the present invention, capacitor 330 is charged between about 3 to 6 times a month (preferably, about 3 times per month). Further, in the present invention, as will also be described below, capacitor 330 is charged for between about 0.5 seconds and 2.5 seconds each time it is charged (preferably, about 0.5 seconds each time it is charged). Thus, on the low end, about 7.5 joules are withdrawn from battery 110 per month (i.e., 0.5 seconds×5 joules/second×3=7.5 joules per month), using the present invention. This is significantly less than the 50 joules per month that are withdrawn using the conventional technique explained above. On the high end, about 75 joules are withdrawn from battery 110 per month (i.e., 2.5 seconds×5 joules/second×6=75 joules per month). However, the inventors of the present invention believe that the drawing of the high end amount of joules in a month would be unlikely, and infrequent if it were to occur.

In an alternate embodiment, for varying battery chemistries, the charge interval may be modified. For example, it might be extended to approximately 20 or even 30 days. For different battery chemistries, testing can be used to empirically determine optimal charge intervals. Furthermore, in another embodiment, a hybrid approach is taken. That is, the battery may occasionally fully charge the capacitor. For example, the battery can periodically (e.g., every 5 to 10 days) provide a partial charge and then less periodically (e.g., every 20 to 60 days) provide a full charge. While this method would use more energy than doing only partial charges, it is still more efficient than conventional methods and has the added advantage of providing fast charge times as a result of well formed capacitors.

Preferred Embodiments of the Present Invention

Figure 7:
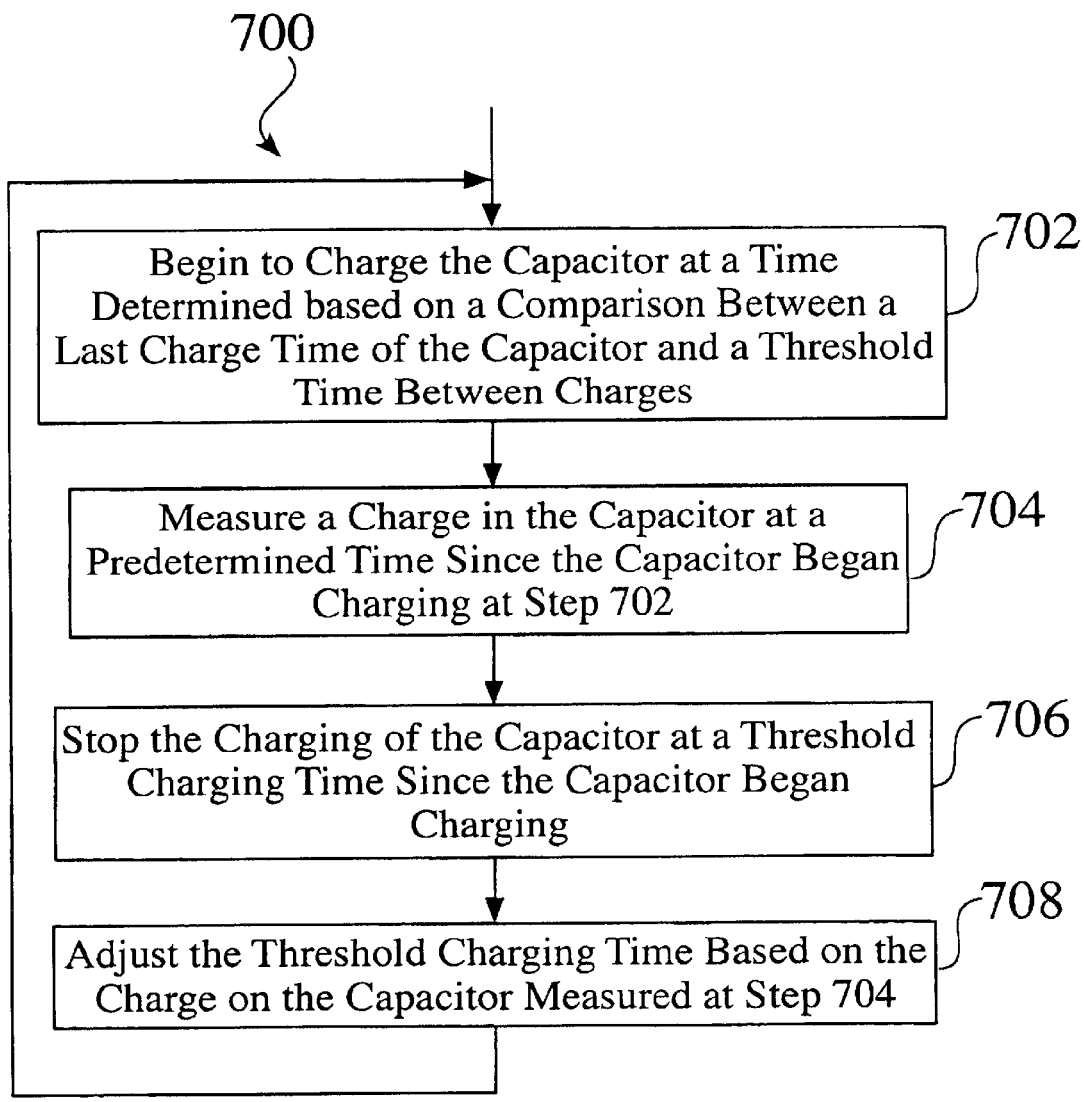
FIG. 7 is a flow diagram useful for describing an overview of the operation of an embodiment of the present invention where a threshold charging time is adjusted.

FIG. 7 illustrates a flow diagram of a method 700 useful for describing an overview of the operation of embodiments of the present invention. At a first step 702, capacitor 330 begins to be charged at a time determined based on a comparison between a time since a last charge of the capacitor and a threshold time between charges. For example, the charging of the capacitor begins when the time since the last charge of the capacitor equals the threshold time between charges. An exemplary threshold time between charges is about 10 days. If this were the case, capacitor 330 would be charged about three times per month. Preferably, the threshold time between charges is set to be between about 5 days and about 10 days. The less frequent the time between charges and the less energy drawn from battery 110 each time capacitor 330 is charged, the longer the life of battery 110 will last.

At a next step 704, a charge on capacitor 330 is measured at a predetermined time (e.g., 0.5 seconds) since the capacitor began charging at step 702. It is noted that stimulation device 10 constantly monitors the voltage on capacitor 330 of shocking circuit 116. Thus, it is well known how to measure or determine a charge on capacitor 330. One possible way of doing this is using a voltmeter in parallel with capacitor 330. As will be described below, this measurement is used to determine whether battery 110 has an abnormally high ESR, and thus would exhibit an unacceptable voltage delay.

Capacitor 330 continues to be charged until a threshold charging time. The threshold charging time specifies the amount of time for which capacitor 330 is charged. More specifically, at a step 706 the charging of capacitor 330 is stopped at the threshold charging time since the capacitor began charging. The threshold charging time is preferably between about 0.5 seconds and 2.5 seconds. After the charging of capacitor 330 stops, the charge is discharged using, for example, a dump circuit. An exemplary dump circuit is explained in the description of FIG. 3.

Next, at a step 708, the threshold charging time is adjusted based on the charge on the capacitor measured at step 704. The threshold charging time is preferably as low as possible to minimize the amount energy drawn from battery 110. Based on the charge on capacitor 330 measured at step 704, it can be determined whether battery 110 has an abnormally high ESR and thus will exhibit an unacceptable voltage delay. For example, if the charge on capacitor 330 measured at step 704 is greater than the threshold charge value, then it is assumed that the passivation film developed on battery 110 is sufficiently low that the threshold charging time can be decreased (to thereby save energy in battery 110). However, if the charge on capacitor 330 measured at step 704 is less than the threshold charge value, then it is assumed that the passivation film developed on battery 110 is sufficiently high that the threshold charging time should be increased. Details of an exemplary embodiment of step 708 are described with reference to FIG. 8.

Figure 8:
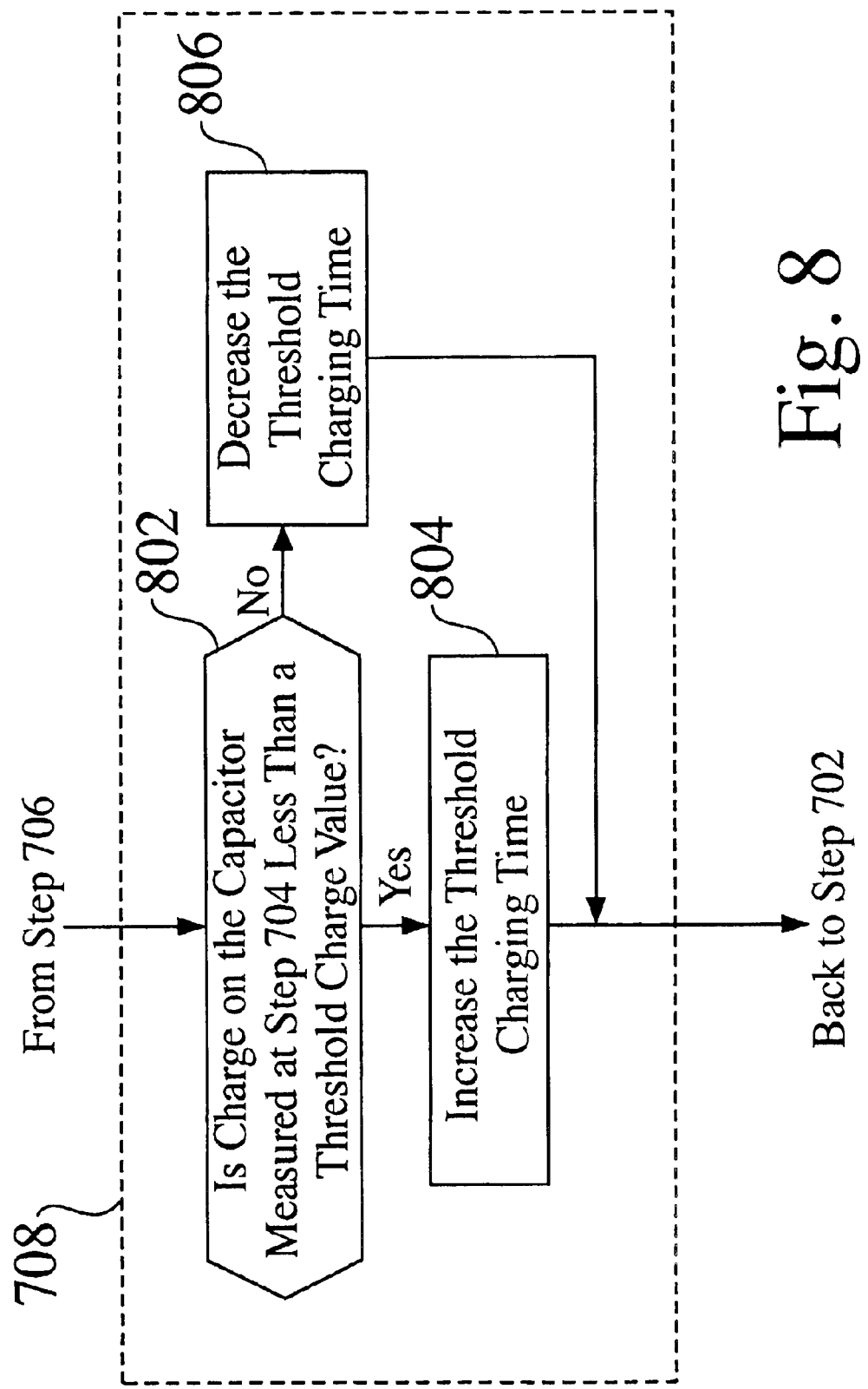
FIG. 8 is a flow diagram that provides additional details of one of the steps of FIG. 7, according to an embodiment of the present invention.

Referring to FIG. 8, at a step 802 there is a determination of whether the charge on capacitor 330 measured at step 704 is less than the threshold charge value (e.g., 130 volts). If the answer to step 802 is NO, then flow goes to a step 806 and there is an assumption that battery 110 is not experiencing voltage delay problems. Accordingly, at step 806 the threshold charging time is decreased. If the answer to step 802 is YES, then flow goes to a step 804 and there is an assumption that battery 110 is experiencing voltage delay problems. Accordingly, at step 804 the threshold charging time is increased.

Preferably, the threshold charge time is not increased above a maximum threshold charging time or below a minimum threshold charging time. The minimum threshold charging time is about 0.5 seconds. The maximum threshold charging time is about 2.5 seconds. Increases and decreases in the threshold charging time can occur in predetermined intervals, although the present invention is not limited to this. An exemplary interval is 0.5 seconds, although the increase interval and the decrease interval need not be equal.

After step 708, flow returns to step 702. Capacitor 330 is not again charged until the threshold time between charges (e.g., 10 days) later. An exception to this is if capacitor 330 is charged for the purpose of delivering a shock to the heart. If this were to occur, then the measurement of time since a last charge of capacitor 330 should be reset.

In FIG. 7, step 706 is shown as occurring prior to step 708. However, it may be preferable to perform step 708 prior to step 706 so that the adjustment to the threshold charging time affects the present charging of the capacitor (i.e., reduces or increases the present charging time). It is noted that the present invention includes either order of steps 706 and 708.

In the above discussed manner, method 700 is used to inhibit voltage delay in battery 110 of stimulation device 10. Preferably, the steps of method 700 only occur when the unloaded voltage of battery 110 is in relatively steep transition region 606. This can be accomplished by only performing the steps when the voltage of battery 110 is between a predetermined unloaded voltage range. This can be measured, for example, using a voltage meter that is in parallel with battery 110. The predetermined unloaded voltage range includes, for example, an upper boundary of about 2.9 volts and a lower boundary of about 2.6 volts. This range occurs after substantially all of Silver within battery 110 is expelled.

As mentioned above, a purpose of the present invention is to inhibit voltage delay in battery 110 (and reforming capacitor 330) using as little energy from battery 110 as possible, thereby maximizing the life of battery 110 while also maintaining it at an ideal state of voltage and current delivery capacity. In method 700, this is accomplished by adjusting the threshold charging time such that it is theoretically just enough to sufficiently burn off the passivation layer on battery 110. In another embodiment, described below with reference to FIG. 9, rather than adjusting the threshold charging time, the threshold time between charges is adjusted.

Figure 9:
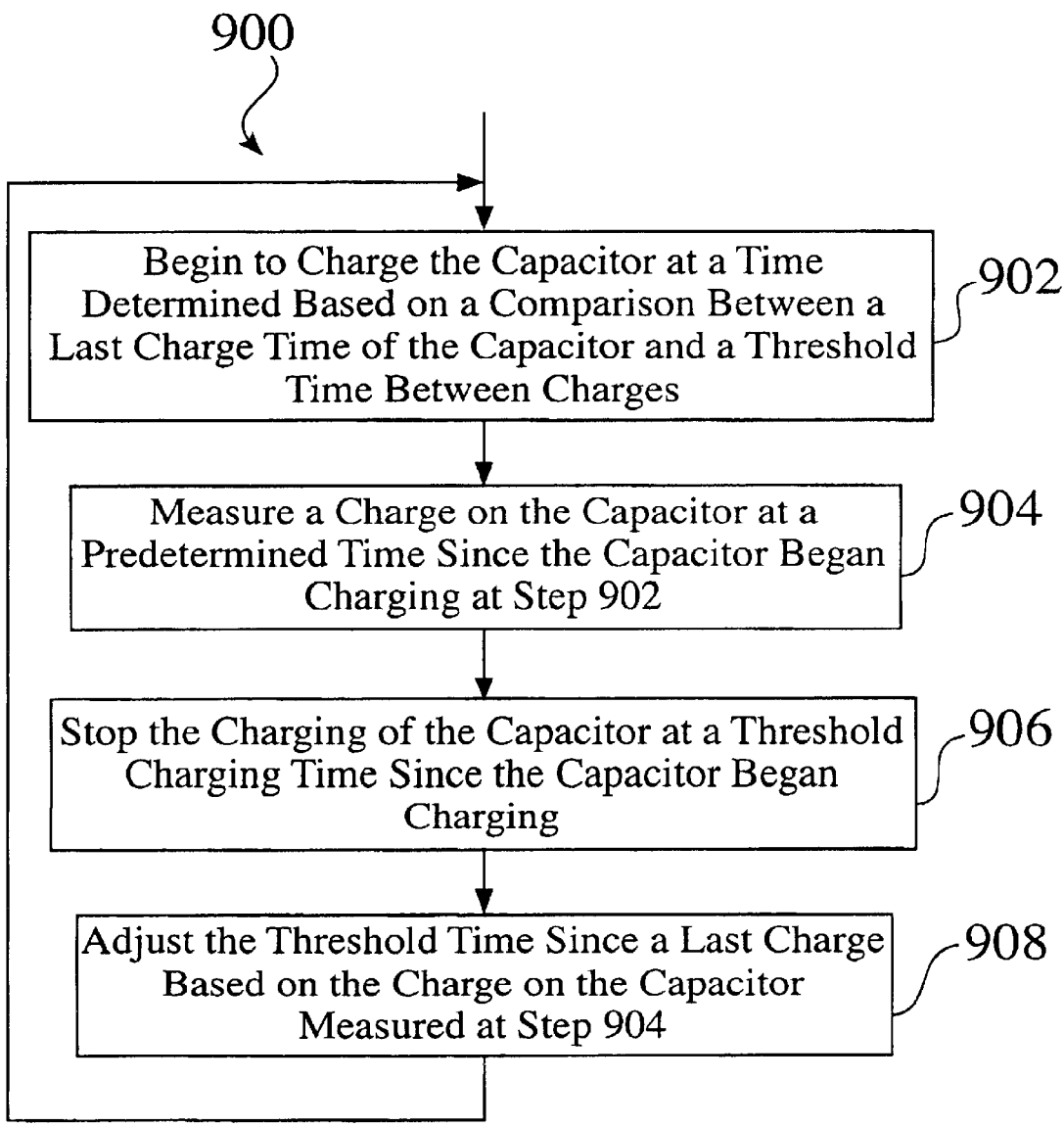
FIG. 9 is a flow diagram useful for describing an overview of the operation of an embodiment of the present invention where a threshold time between charges is adjusted.

FIG. 9 illustrates a flow diagram of a method 900 useful for describing an overview of the operation of alternative embodiments of the present invention. A review of the flowchart shows that steps 902, 904 and 906 are the same as steps 702, 704 and 706, respectively. Accordingly, these steps will not be described again. The threshold charging time in this embodiment is constant. An exemplary threshold charging time is about 2.0 seconds.

At a step 908, the threshold time between charges is adjusted based on the charge on the capacitor measured at step 904. The threshold time between charges is preferably as high as possible to minimize the amount energy drawn from battery 110. Based on the charge on capacitor 330 measured at step 904, it can be determined whether battery 110 has an abnormally high ESR, and thus will exhibit an unacceptable voltage delay. If the charge on capacitor 330 measured at step 904 is greater than the threshold charge value, then it is assumed that the passivation film developed on battery 110 is sufficiently low that the threshold time between charges can be increased (to thereby save energy in battery 110). If the charge on capacitor 330 measured at step 904 is less than the threshold charge value, then it is assumed that the passivation film developed on battery 110 is sufficiently high that the threshold time between charges should be decreased. Details of an exemplary embodiment of step 908 are described with reference to FIG. 10.

Figure 10:
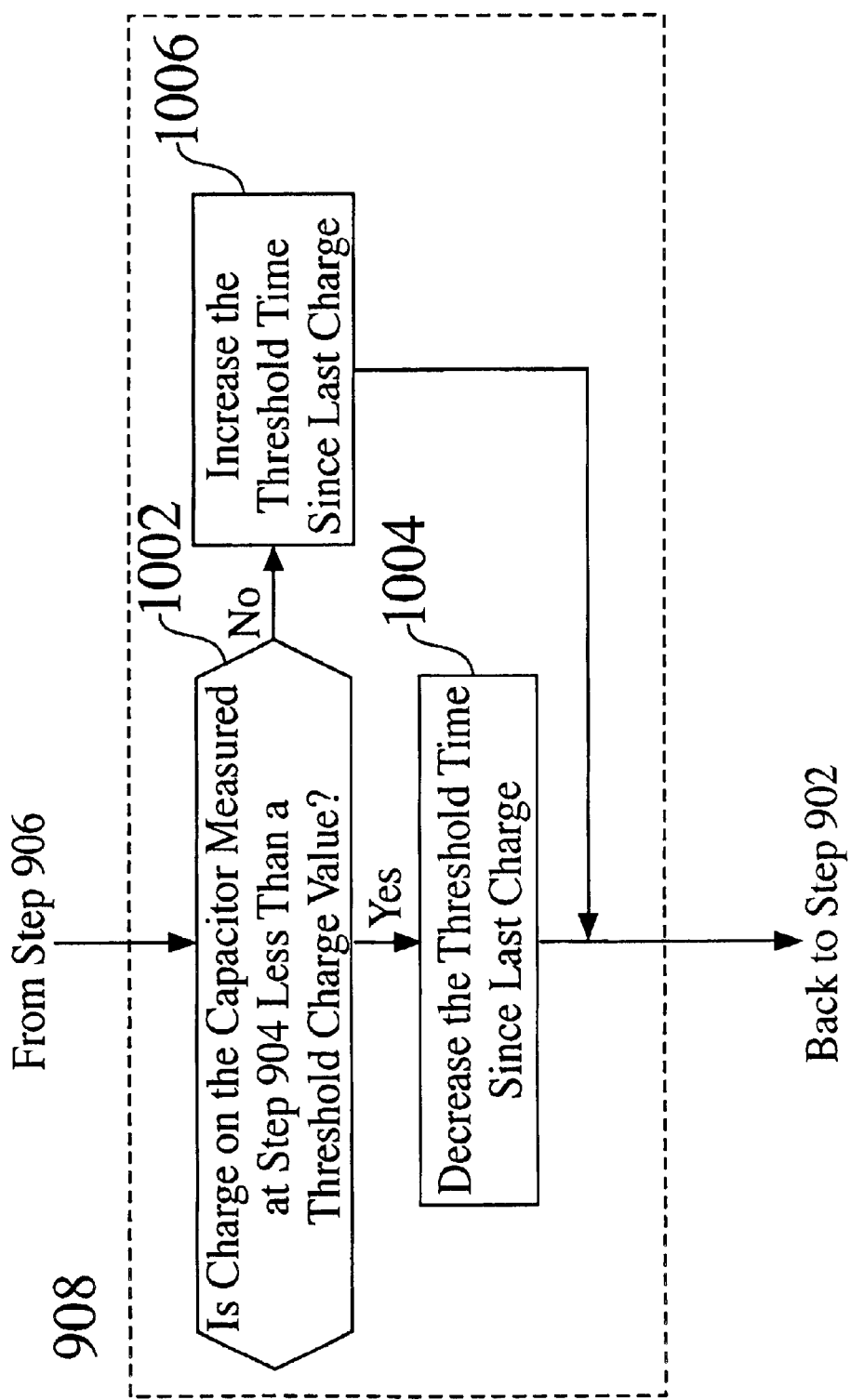
FIG. 10 is a flow diagram that provides additional details of one of the steps of FIG. 9, according to an embodiment of the present invention.

Referring to FIG. 10, at a step 1002 there is a determination of whether the charge on capacitor 330 measured at step 904 is less than the threshold charge value (e.g., 130 volts). If the answer to step 1002 is NO, then flow goes to a step 1006 and there is an assumption that battery 110 will not experience voltage delay problems. Accordingly, at step 1006 the threshold time between charges is increased. If the answer to step 1002 is YES, then flow goes to a step 1004 and there is an assumption that battery 110 may experience an unacceptable voltage delay. Accordingly, at step 1004 the threshold time between charges is decreased.

Preferably, the threshold time between charges is not increased above a maximum threshold time between charges or below a minimum threshold time between charges. The minimum threshold time between charges is about 5 days. The maximum threshold time between charges is about 10 days. Increases and decreases in the threshold time between charges can occur in predetermined intervals, although the present invention is not limited to this. An exemplary interval is 1 day, although the increase interval and the decrease interval need not be equal.

After step 908, flow returns to step 902. Capacitor 330 is not again charged until the threshold time between charges has elapsed (e.g., between about 5 and 10 days). An exception to this is if capacitor 330 is charged for the purpose of delivering a shock to the heart. If this were to occur, then the measurement of the time since a last charge should be reset.

In the above discussed manner, method 900 is used to inhibit voltage delay in battery 110 of stimulation device 10. Similar to method 700, preferably the steps of method 900 only occur when the unloaded voltage of battery 110 is in relatively steep transition region 606. This can be accomplished by only performing the steps when the voltage of battery 110 is between a predetermined unloaded voltage range.

As mentioned above, a purpose of the present invention is to inhibit voltage delay in battery 110 (and reform capacitor 330) using as little energy from battery 110 as possible, thereby maximizing the life of battery 110 while also maintaining it at an ideal state of voltage and current delivery capacity. In method 900, this is accomplished by adjusting the threshold time between charges. In the embodiment described above with reference to FIG. 7, the threshold charging time is adjusted. In still another embodiment, both the threshold time between charges and the threshold charging time are adjusted.

The previous description of the preferred embodiments is provided to enable any person skilled in the art to make or use the present invention. While the invention has been particularly shown and described with reference to preferred embodiments thereof, it will be understood by those skilled in the art that various changes in form and details may be made therein without departing from the spirit and scope of the invention.

Furthermore, some embodiments of the present invention discussed above have only been described as methods with reference to a flow chart. The present invention is also directed to devices (also referred to as apparatuses) that perform the features discussed above. For example, the present invention is also directed to a microprocessor (e.g., microprocessor 60) that performs features of the present invention. Additionally, the present invention is also directed to an implantable device (e.g., device 10) that includes a microprocessor for performing such features. Further, the present invention is also directed to systems that perform the features discussed above. Such a system can be, for example, an external processor in communications with a microprocessor of an implantable device.

What is claimed is:

1. For use with an implantable cardiac stimulation device including a capacitor for storing charges used to shock a heart and a battery for charging the capacitor, a method for inhibiting battery voltage delay comprising the steps of:

(a) beginning to charge the capacitor at a time determined based on a comparison between a time since a last charge of the capacitor and a threshold time between charges;

(b) measuring a charge on the capacitor at a predetermined time since the capacitor began charging at step (a);

(c) stopping the charging of the capacitor at a threshold charging time since the capacitor began charging; and (d) adjusting the threshold charging time based on the charge on the capacitor measured at step (b).

2. The method of claim 1, wherein step (a) comprises charging the capacitor, using the battery, when the time since the last charge of the capacitor equals the threshold time between charges.

3. The method of claim 1, wherein step (d) comprises:

(d.1) increasing the threshold charging time if the charge on the capacitor measured at step (b) is less than a threshold charge value; and (d.2) decreasing the threshold charging time if the charge on the capacitor measured at step (b) is greater than the threshold charge value.

4. The method of claim 1, wherein step (d) comprises:

(d.1) increasing the threshold charging time if
the charge on the capacitor measured at step (b) is less than a threshold charge value, and
the threshold charging time is less than a maximum threshold charging time; and (d.2) decreasing the threshold charging time if
the charge on the capacitor measured at step (b) is greater than the threshold charge value, and
the threshold charging time is greater than a minimum threshold charging time.

5. The method of claim 4, wherein:
the threshold charging time is not increased above the maximum threshold charging time; and
the threshold charging time is not decreased below the minimum threshold charging time.

6. The method of claim 5, wherein:
the minimum threshold charging time is about 0.5 seconds; and
the maximum threshold charging time is about 2.5 seconds.

7. The method of claim 1, wherein step (d) comprises:

(d.1) increasing the threshold charging time by an increase interval of about 0.5 seconds if the charge on the capacitor measured at step (b) is less than a threshold charge value; and (d.2) decreasing the threshold charging time by a decrease interval of about 0.5 second if the charge on the capacitor measured at step (b) is greater than the threshold charge value.

8. The method of claim 1, further comprising repeating steps (a) through (d).

9. The method of claim 1, wherein steps (a) through (d) only occur when an unloaded voltage of the battery is between a predetermined unloaded voltage range.

10. The method of claim 9, wherein the predetermined unloaded voltage range includes:
an upper boundary of about 2.9 volts; and
a lower boundary of about 2.6 volts.

11. The method of claim 1, wherein steps (a) through (d) only occur during the relatively steep region of an unloaded voltage curve associated with the battery.

12. The method of claim 1, further comprising the step:

(e) adjusting the threshold time between charges based on the charge on the capacitor measured at step (b).

13. An implantable cardiac stimulation device, comprising:

a capacitor to store charges;

a battery to charge the capacitor;

a controller to control the charging of the capacitor by the battery at a time determined based on a comparison between a time since a last charge of the capacitor and a threshold time between charges;

means for measuring a charge on the capacitor at a predetermined time since the capacitor began charging;

means for stopping charging of the capacitor at a threshold charging time since the capacitor began charging; and means for adjusting the threshold charging time based on the charge on the capacitor at the predetermined time.

14. The device of claim 13, wherein the means for measuring comprises a volt meter.

15. The device of claim 13, wherein the means for adjusting the threshold charging time is part of the controller.

* * * * *